United States Patent
Rivolta et al.

(10) Patent No.: US 7,745,496 B2
(45) Date of Patent: Jun. 29, 2010

(54) PROCESS FOR PREPARING HALOGENOALKYLNITRATES

(75) Inventors: Romano Rivolta, Antibes (FR); Peter Finlander, Hoersholm (DK)

(73) Assignee: Nicox S.A., Valbonne (FR)

( * ) Notice: Subject to any disclaimer, the term of this patent is extended or adjusted under 35 U.S.C. 154(b) by 173 days.

(21) Appl. No.: 11/667,970

(22) PCT Filed: Nov. 9, 2005

(86) PCT No.: PCT/EP2005/055865
§ 371 (c)(1),
(2), (4) Date: May 17, 2007

(87) PCT Pub. No.: WO2006/056535
PCT Pub. Date: Jun. 1, 2006

(65) Prior Publication Data
US 2008/0004463 A1    Jan. 3, 2008

(30) Foreign Application Priority Data
Nov. 25, 2004   (EP) ................... 04292785

(51) Int. Cl.
*A61K 31/02*   (2006.01)
*C07C 291/02*  (2006.01)
(52) U.S. Cl. ................ 514/727; 558/480
(58) Field of Classification Search .......... 558/480
See application file for complete search history.

(56) References Cited

U.S. PATENT DOCUMENTS

2005/0192346 A1   9/2005   Shi et al.

FOREIGN PATENT DOCUMENTS

WO   WO 2004/020384 A1   3/2004
WO   WO 2004/020385 A1   3/2004

OTHER PUBLICATIONS

Kawashima et al; "*Synthesis and Pharmacological Evaluation of (Nitrooxy)alkyl Apovincaminates*", J Med. Chem., 1993, pp. 815-819, XP002362995, p. 818, col. 2, line 2-p. 819, col. 1, line 15, compounds 18,19,21-24 vol. 36, Japan.
Svetlakov et al; "*Nitrolysis of organic halides: II. Nitrolysis of Alkyl halides, and the mechanism of the reaction*", Zhurnal Organicheskoi Khimii, 1968, pp. 1893-1899, XP008058467 col. 8, line 32; table 3, vol. 4 No. 11, Japan.

*Primary Examiner*—Rebecca L Anderson
*Assistant Examiner*—Shawquia Young
(74) *Attorney, Agent, or Firm*—Arent Fox LLP

(57) ABSTRACT

A process for preparing a compound of formula (I)

$$X\text{-}(CH_2)_n\text{-}ONO_2 \quad (I)$$

wherein:
X is a halogen atom selected from Cl, Br, I;
n is an integer from 3 to 6;
said process comprising the slow addition of a compound of formula (II)

$$X\text{-}(CH_2)_n\text{-}OH \quad (II)$$

wherein X and n are as defined above to a nitrating agent selected from the group consisting of concentrated nitric acid/concentrated sulfuric acid (sulfonitric mixture), nitric acid alone, $NaNO_2$ in trifluoroacetic acid, nitronium salts such as $NO_2BF_4$ and an organic solvent selected from the group consisting of $CH_2Cl_2$, $CHCl_3$, $CCl_4$, perfluorohexane, perfluoroheptane. The invention refers also to solutions containing: a compound of general formula (I) and a solvent selected from the group consisting of $CH_2Cl_2$, $CHCl_3$, $CCl_4$, perfluorohexane, perfluoroheptane, characterized in that the compound of formula (I) is present in a concentration not higher than 20% by weight.

8 Claims, No Drawings

PROCESS FOR PREPARING HALOGENOALKYLNITRATES

CROSS-REFERENCE TO RELATED APPLICATION

This application is a National Stage entry of International Application No. PCT/EP2005/055865, filed Nov. 9, 2005, the entire specification, and claims of which are incorporated herewith by reference.

The present invention refers to a process for preparing halogenoalkylnitrates, in particular 4-bromobutylnitrate, and to stable solutions containing them.

4-Bromobutylnitrate is a thermally unstable oily liquid which is used in the preparation of nitrooxyalkylesters of pharmacologically active carboxylic acids (WO 04/020384, WO 04/020385). 4-Bromobutylnitrate, not diluted in solvents, is added to a solution/suspension of pharmacologically active carboxylic acid, such as naproxen, ferulic acid etc. 4-Bromobutylnitrate is prepared by nitration with sulfonitric mixture of 4-bromo-1-hydroxybutane (Chem. Pharm. Bull., 1993,41,1040). The reaction is carried out by adding 4-bromo-1-hydroxybutane to neat sulfonitric mixture, that is in the absence of solvents or diluents. The reaction is limited to laboratory scale because the process is potentially explosive, due to sudden increases of temperature and development of gases.

The end product, 4-bromo-butylnitrate, is purified by distillation under vacuum. The neat product is potentially explosive and it is prepared and used soon after its preparation.

It has now been unexpectedly found that solutions of halogenoalkylnitrates in particular organic solvents are stable and are not explosive and can been obtained by a thermally controllable nitration which avoids gas evolution.

The present invention refers to a solution containing:
a) a compound of general formula (I)

$X$-$(CH_2)_n$-$ONO_2$ (I)

wherein:

X is a halogen atom selected from Cl, Br and I, n is an integer from 3 to 6 and b) a solvent selected from the group consisting of $CH_2Cl_2$, $CHCl_3$, $CCl_4$, perfluorohexane, perfluoroheptane; characterized in that the compound of formula (I) is present in a concentration not higher than 20% by weight. Said solutions are stable and not explosive in comparison with the pure products. Explosive properties were evaluated in "Heating under confinement" (flame effect) test and "Drop Hammer" test (see experimental section). Pure m-dinitrobenzene was used as reference sample. The solutions of the invention can be handled and transported without risk of explosion. Another advantage is that said solutions can be used as such in the esterification reactions of pharmacologically active carboxylic acids.

Preferred compounds of formula (I) as defined above are those wherein n is 4 and/or X is Br.

Preferred solvents are $CH_2Cl_2$, $CHCl_3$, $CCl_4$, perfluorohexane, perfluoroheptane The most preferred is $CH_2Cl_2$.

Preferred solutions are those wherein the compound of formula (I) as above defined is present in a concentration from 10% to 20% by weight.

A further object of the present invention is a process for preparing a compound of formula (I) as above defined, said process comprising the slow addition of a compound of formula (II)

$X$-$(CH_2)$-$OH$ (II)

wherein X and n are as above defined to a nitrating agent selected from the group consisting of concentrated nitric acid/concentrated sulfuric acid (sulfonitric mixture), nitric acid alone, $NaNO_2$ in trifluoroacetic acid, nitronium salts such as $NO_2BF_4$ and an organic solvent selected from the group consisting of $CH_2Cl_2$, $CHCl_3$, $CCl_4$, perfluorohexane, perfluoroheptane.

Said process is preferably directed to the preparation of a compound of formula (I) as above defined wherein X is Br and/or n is 4.

The preferred solvent used in the process are $CH_2Cl_2$, $CHCl_3$, $CCl_4$. The most preferred solvent is $CH_2Cl_2$.

The preferred molar ratio of compound of formula (II): nitric acid in the sulfonitric mixture is from 0.2 to 1.

The preferred molar ratio of nitric acid: sulfuric acid in the sulfonitric mixture is from 0.2 to 1.5.

The reaction is preferably carried out at a temperature ranging from −10° C. to +20° C.

Calorimetric study of the nitration reaction, using RC1 calorimeter, shows that the reaction is clearly exothermic.

The enthalpy of the nitration of 4-bromobutanol, carried out in the biphasic system $CH_2Cl_2/H_2SO_4/HNO_3$ at 5° C., by dosing the total amount of 4-bromo-1-hydroxybutane is −161.7 KJ/kg, but the heat flow rate, as determined, is dosing controlled.

After usual work up the solution of halogenoalkylnitrate is separated and is concentrated under vacuum to the desired concentration.

Halogenoalkylnitrates yield, determined in solution, is higher than 80%, as high as 95%. The product solution is sufficiently pure to be used, without further purification, in the subsequent preparation of nitrooxyalkylesters of pharmacologically active carboxylic acids.

EXAMPLE 1

Preparation of a solution of 4-bromobutylnitrate in $CH_2Cl_2$

A 1 L, three-necked round bottomed flask, equipped with a thermometer, a dropping funnel, and a mechanical stirrer was charged with 98% sulfuric acid (275 g, 2.75 mol) and methylene chloride (275 ml, d 1.325, 364.4 g,). The mixture was cooled to 2° C. and kept at this temperature, while 100% nitric acid (173.0 g, 2.75 mol) was added over 15 minutes. 4-Bromo-1-hydroxybutane (211.0 g, 1.38 mol) was added at 2° C. over 45 minutes to the reaction mixture.

The reaction mixture was stirred for further 15 minutes, added with methylene chloride (453 ml, 600.0 g ) and then poured in cooled water (2750 g). The aqueous phase was kept at 5-10° C., while the reaction mixture was added over 10 minutes. The lower organic phase was separated. The upper aqueous phase was extracted with methylene chloride (275 ml; 364.4 g). The combined methylene chloride extracts were stirred with water (275 ml, and the pH of the mixture was adjusted from 0.6 to 6 by addition of 6% sodium hydrogen carbonate (100 ml). The organic extract was separated and concentrated under vacuum at room temperature to give a 20% solution of 4-bromobutylnitrate ( 232.7 g, 85% yield ) in methylene chloride ( 930.8 g).

EXAMPLE 2

Preparation of a solution of 4-bromobutylnitrate in $CH_2Cl_2$ (alternative synthesis)

A 1 L, three-necked round bottomed flask, equipped with a thermometer, a dropping funnel, and a mechanical stirrer was charged with 98% sulfuric acid (275 g,2.75 mol) and methylene chloride (728 ml, d 1.325, 964.4 g). The mixture was cooled to 2° C. and kept at this temperature, while 100% nitric acid (173.0 g, 2.75 mol) was added over 15 minutes.

The reaction mixture was now an emulsion of two colourless liquid phases. 4-Bromo-1-hydroxybutane (211.0 g, 1.38 mol) was added at 2° C. over 45 minutes.

The reaction mixture was stirred for further 15 minutes, and then poured in cooled water (2750 g). The water was kept at 5-10° C., while the reaction mixture was added over 10 minutes. The lower organic phase was separated. The upper aqueous phase was extracted with methylene chloride (275 ml; 364.4 g). The combined methylene chloride extracts were stirred with water (275 ml, and the pH of the mixture was adjusted from 0.6 to 6 by addition of 6% sodium hydrogen carbonate(100 ml). The organic extract was separated and concentrated under vacuum at room temperature to give a 20% solution of 4-bromobutylnitrate (232.7 g, 85% yield) in methylene chloride (930.8 g).

EXAMPLE 3

Synthesis of (E)-3-(4-hydroxy-3-methoxyphenyl)-2-propenoic acid 4-(nitrooxy)butyl ester a) Preparation of the Sodium Salt of (E)-3-(4-hydroxy-3-methoxyphenyl)-2-propenoic acid (Ferulic Acid)

Synthesis of Potassium (E)-3-(4-hydroxy-3-methoxyphenyl)-2-propenoate

A 500 ml three-necked round bottomed flask, equipped with a thermometer, an addition funnel, a mechanical stirrer, maintained under nitrogen atmosphere, was charged with (E)-3-(4-Hydroxy-3-methoxyphenyl)-2-propenoic acid (ferulic acid) (19.4 g, 100 mmol) and methanol (150 ml). The mixture was stirred till a limpid solution was obtained. A 85% solution of potassium hydroxide in methanol (6,6 g, 100 mmol in 50 ml methanol) was added to the obtained solution. The temperature was allowed to increase till 40° C. The formation of an insoluble crystalline product was observed.

Toluene (250 ml) was added under stirring and the obtained suspension was cooled to 10° C. The insoluble product was filtered and washed with toluene (50 ml) and then with hexane (2×50 ml).The product was dried under reduced pressure to give 20.96 g (89% yield) of a yellowish powder.

b) Esterification Reaction

A mixture of potassium (E)-3-(4-hydroxy-3-methoxyphenyl)-2-propenoate (2.07 g; 9 mmol), obtained in the previous step, DMF (8.3 g), KI (0.5 g) and a 20% w/w solution (82.5 g) of 4-bromobutylnitrate (16.5 g; 16.7 mmol) in $CH_2Cl_2$ is heated under stirring to 40° C. and kept at this temperature under stirring for 136 h. After work up, (E)-3-(4-hydroxy-3-methoxyphenyl)-2-propenoic acid 4-(nitrooxy)butyl ester was obtained in 70% yield.

EXAMPLE 4

Sensitivity to Impact Test of 4-bromobutylnitrate pure and Dilute in $CH_2Cl_2$ at Different Concentration The test for the sensitivity to impact was carried out according the following procedure.

The apparatus (called drop hammer) consists of a base, a graduated scale, two rails, a weight, a sample holder and an impactor. The 5 kg weight flows vertically from a height of 200 cm maximum on the rails and falls over the impactor. It conveys the impact to the sample charged in the sample holder on the base. The sample holder is made of two coaxial solid cylinders in steel and laid upon a hollow steel cylinder. The solid cylinders have a diameter of 10 mm and a height of 10 mm. The hollow cylinder has an external diameter of 22 mm, a hole of 10 mm, and a height of 16 mm. This apparatus tests 40 mm$^3$ of sample. The weight falls on the impactor from 1 to 200 cm until a reaction is observed (bang, smoke, fire, sparks). Same samples decompose under impact without bang, smoke, fire or sparks visible only by the complete decomposition of the sample when the die is opened.

The results of the tests are reported in Table 1. m-dinitrobenzene was used as reference compound.

TABLE 1

| SAMPLE | IMPACT ENERGY (J) | OBSERVATIONS |
| --- | --- | --- |
| Pure 4-bromobutylnitrate | 25 | Reaction with smoke |
| Pure dinitrobenzene | 40 | Decomposes |
| 30% w/w 4-bromobutylnitrate in $CH_2Cl_2$ | 40 | Reaction with hange of color |
| 20% w/w 4-bromobutylnitrate in $CH_2Cl_2$ | 90 | Decomposition without bang, smoke, fire, sparks |

GC analysis confirms visual observation of the "Drop Hammer" test.

EXAMPLE 5

Sensitivity to the Test "Heating under Confinement" (Flame Effect) of 4-bromobutylnitrate Pure and Dilute in $CH_2Cl_2$ at Different Concentration The test is used to determine the sensitiveness of a material to the effect of intense heat under vented confinement. In this test, the material is placed in a steel container with an orifice plate. The test apparatus is then placed in a protective steel box, and heated at a specified rate. A series of trials is conducted using different sizes of orifices. A "go" reaction is determined by examining the container. It must be broken in more than two pieces.

A sample consisting of 20% w/w 4-bromobutylnitrate in $CH_2Cl_2$ was subjected to the above reported test. The result of the test was negative, in line with the result obtained with the "Drop Hammer" test.

The invention claimed is:

1. A solution containing:
  a) a compound of general formula (I)

$$X\text{-}(CH_2)_n\text{-}ONO_2 \qquad (I)$$

wherein:
X is a halogen atom selected from the group consisting of: Cl, Br, and I;
n is an integer from 3 to 6; and
b) a solvent selected from the group consisting of:
$CH_2Cl_2$, $CHCl_3$, $CCl_4$, perfluorohexane, and perfluoroheptane;
wherein the compound of formula (I) is present in a concentration not higher than 20% by weight.

2. A solution according to claim 1 containing a compound of formula (I) wherein n is 4.

3. A solution according to claim 1 containing a compound of formula (I) wherein X is Br.

4. A solution according to claim 1 wherein the solvent is $CH_2Cl_2$.

5. A solution according to claim 1 wherein the compound of formula (I) is present in a concentration from 10% to 20% by weight.

6. A process for preparing a compound of formula (I) as defined in claim 1, said process comprising the slow addition of a compound of formula (II)

$$X\text{-}(CH_2)_n\text{-}OH \qquad (II)$$

wherein X and N are as defined in claim 1 to a nitrating agent selected from the group consisting of concentrated nitric acid/concentrated sulfuric acid (sulfonitric mixture), nitric acid alone, $NaNO_2$ in trifluoroacetic acid, nitronium salts such as NO2BF4 and an organic solvent selected from the group consisting of $CH_2Cl_2$, $CHCl_3$, $CCl_4$, perfluorohexane, perfluoroheptane.

7. A process according to claim 6 for preparing a compound of formula (I) wherein X is Br.

8. A process according to claim 6 wherein the organic solvent is $CH_2Cl_2$.

* * * * *